US008784366B2

(12) United States Patent
Robinson (10) Patent No.: US 8,784,366 B2
(45) Date of Patent: Jul. 22, 2014

(54) INTRAVASCULAR CEREBRAL CATHETER DEVICE AND METHOD OF USE

(76) Inventor: Joe Sam Robinson, Macon, GA (US)

( * ) Notice: Subject to any disclaimer, the term of this patent is extended or adjusted under 35 U.S.C. 154(b) by 616 days.

(21) Appl. No.: 12/876,786

(22) Filed: Sep. 7, 2010

(65) Prior Publication Data

US 2010/0331813 A1 Dec. 30, 2010

Related U.S. Application Data

(63) Continuation of application No. PCT/US2009/038071, filed on Mar. 24, 2009.

(60) Provisional application No. 61/038,922, filed on Mar. 24, 2008.

(51) Int. Cl.
*A61M 31/00* (2006.01)
*A61M 5/00* (2006.01)
*A61M 25/00* (2006.01)

(52) U.S. Cl.
USPC ............................................ 604/65; 604/264

(58) Field of Classification Search
USPC ................ 604/65, 66, 67, 118, 264, 265, 523
See application file for complete search history.

(56) References Cited

U.S. PATENT DOCUMENTS

| 5,305,745 | A | * | 4/1994 | Zacouto | 600/324 |
| 5,333,609 | A | * | 8/1994 | Bedingham et al. | 600/339 |
| 5,879,499 | A | * | 3/1999 | Corvi | 156/175 |
| 6,506,146 | B1 | | 1/2003 | Mohl | |
| 6,622,367 | B1 | * | 9/2003 | Bolduc et al. | 29/447 |
| 2001/0039440 | A1 | | 11/2001 | Lasheras et al. | |
| 2003/0036773 | A1 | * | 2/2003 | Whitehurst et al. | 607/3 |
| 2003/0093027 | A1 | | 5/2003 | McGuckin, Jr. et al. | |
| 2004/0127813 | A1 | * | 7/2004 | Schwamm | 600/561 |
| 2007/0249997 | A1 | | 10/2007 | Goodson, IV et al. | |
| 2008/0065192 | A1 | | 3/2008 | Berglund | |

FOREIGN PATENT DOCUMENTS

WO    WO2007/093778 A1    8/2007

OTHER PUBLICATIONS

European Supplementary Search Report for EP Application No. 09725135 mailed Jul. 19, 2011 (5 pages).
International Search Report for PCT/US2009/38071 dated May 4, 2009 (1 page).

* cited by examiner

*Primary Examiner* — Kevin C Sirmons
*Assistant Examiner* — Shefali Patel
(74) *Attorney, Agent, or Firm* — Sutherland Asbill & Brennan LLP (57) ABSTRACT

Cerebral catheter devices and methods for use are provided. The catheter devices provided may include an anti-thrombotic agent coating on an exterior surface. The catheter devices may include unique tip configurations to allow improved fluid delivery capabilities. Further, the catheter devices may also or alternatively include one or more sensor devices in communication with a controller that allow automatically adjusting a delivery of a therapeutic fluid, for example a vasodilator, in response to a condition sensed by the catheter devices, such as increased pressure. Moreover, the catheter devices may also be used in conjunction with blood flow transducers to detect and timely prevent and treat vasospasms or other conditions. Methods for preventing and treating vasospasm, neoplasm, or other pathological conditions while prolonged using the catheter devices are also provided.

25 Claims, 4 Drawing Sheets

INTRAVASCULAR CEREBRAL CATHETER DEVICE AND METHOD OF USE

CROSS-REFERENCE TO RELATED APPLICATIONS

This application is a continuation of PCT/US2009/038071 filed on Mar. 24, 2009, which claims priority benefit of U.S. Provisional Application Nos. 61/038,922, filed Mar. 24, 2008, the entire contents of which are incorporated by reference herewith.

FIELD OF THE INVENTION

The present invention relates generally to medical devices, and more particularly to cerebral intravascular catheter devices, and methods of use, for treating cerebral vasospasms and neoplasms, particularly brain glioblastomas.

BACKGROUND OF THE INVENTION

Catheters have many medical uses. Among these uses are delivery of intravenous fluids, administering chemotherapy to a particular organ or site, and to assist in cardiac procedures and for treating coronary artery deficiencies. Catheters are also being used during neurosurgical procedures for the treatment of cerebral vasospasms, which may lead to cerebral ischemic.

However, in any of the above-described uses of catheters, thrombosis and the development of embolisms are a concern when used for extended durations. Embolic phenomenon, which may result from thrombosis, can lead to tissue damage. Maintaining catheterization for extended durations carries significant advantages, such as making available more types of treatment and medicines to the patient, broadening the types of conditions that may be treated rather than by ways of more invasive procedures, improving the effectiveness of treatment due to longer treatment durations, and adjusted treatment cycles, for example.

Avoiding thrombosis or embolic phenomena are particularly important in the treatment of cerebral vasospams. It has been shown that intravascular infusion of verapamil and other substances can minimize cerebral vasospasm. Unfortunately, the catheter cannot be left in situ for a long period of time to treat this relatively chronic condition, thus, suboptimal drug delivery results.

Accordingly, there exists a need for improved catheter devices and methods for using the same. More specifically, there exists a further need for neurological or cerebral intravascular catheter devices and methods for treating cerebral vasospasms and avoiding thrombosis or embolic phenomenon before, during, and after neurosurgery.

SUMMARY OF THE INVENTION

Catheter devices, particularly neurological or cerebral intravascular catheter devices, and methods of use for preventing and/or treating vasospasm, neoplasm, thrombosis or other embolic phenomenon, as well as catheter-induced infections are provided. In certain embodiments, the intravascular catheter devices provided for neurosurgery or brain surgery or other physiological or pathological situations, may be coated on the exterior surface with a matrixes with protein or other substances, such as an anti-thrombotic agent and/or vasodilator. In other embodiments, the intravascular catheter devices may include unique distal tip configurations to allow for improved fluid or drug delivery capabilities to timely release therapeutic fluid containing one or more therapeutic agents for desired treatment. In one embodiment, the therapeutic agent is an anti-thrombosis agent or anticoagulant that would minimize the development of thrombosis and thus diminish the danger of embolic tissue damage. In yet another embodiment, the therapeutic agent is an antibiotic that would treat catheter-induced infection. In yet another embodiment, the therapeutic agent is a chemotherapeutic agent for treating neoplasms. In certain embodiments, the catheter device is configured for insertion into the neural vasculature.

In further embodiments, the intravascular catheter devices may also, or alternatively, include one or more sensor devices in communication with a controller that allow automatically adjusting the delivery of a therapeutic fluid, for example, a vasodilator, in response to a condition sensed by a sensor device of the catheter. In further embodiments, the intravascular catheter devices may be used in conjunction with external monitoring devices, such as a blood flow transducer, to monitor velocity in blood vessels and provide real time vasospasm detection, therefore, allowing time release or delivery of a therapeutic agent to prevent vasospasms, thrombosis, or other embolic phenomenon.

The invention provides a catheter device that allows for prolonged insertion and treatment by including an anti-thrombotic agent or anticoagulant coating to reduce the likelihood of causing thrombosis. In another aspect, the invention includes providing a catheter with sensors that allow sensing certain conditions at or near the procedure site, which further allow a controller to adjust the delivery of a medicinal agent, such as a vasodilator. Accordingly, a catheter device including one or more sensors of this type allow for quick detection of vasospasm activities and immediate treatment thereof.

According to one embodiment of the invention, a catheter device is provided having a distal end and a proximal end, and also having at least one lumen extending from the proximal end to the distal end of the elongate catheter body. An anti-thrombotic agent may be deposited on at least part of the exterior surface of the elongate catheter body. In an exemplary embodiment, the anti-thrombotic agent comprises a coating applied to substantially the entire exterior surface of the elongate catheter body, or alternatively, the anti-thrombotic agent comprises a coating applied to a portion of the elongate catheter body extending proximally from the distal end. Yet further, the anti-thrombotic agent may be at least partially impregnated into the material comprising the elongate catheter body. In another example embodiment, the anti-thrombotic agent may be time releasable. Another aspect of this embodiment may include an anti-thrombotic agent coating at least partially on the interior surface of the catheter within the lumen.

According to another examplary embodiment, the catheter device may include an elongate catheter body having a distal end and a proximal end, and also having at least one lumen extending from the proximal end to the distal end of the elongate catheter body. Further, in this embodiment, a perforated tip may be affixed to the distal end of the elongate catheter body. The perforated tip may include a plurality of perforated orifices extending through the perforated tip and in fluid communication with the lumen or lumens. In one embodiment, the distal catheter may be placed at the most distal part of the internal carotid artery.

Another aspect of this embodiment may include the catheter device having a first and a second lumen extending from the proximal end to the distal end of the elongate catheter body, wherein the perforated tip further comprises at least one central orifice in communication with the first lumen, and wherein the plurality of perforated orifices are in fluid communication with the second lumen. In this example, a secondary medical device may be passed through the first lumen and the at least one central orifice. For example, the secondary medical device may include a guide wire or a balloon.

Another aspect of this embodiment may include the catheter device having at least one fluid that is delivered through the at least one lumen and the plurality of perforated orifices. The fluid may be, for example, a saline solution or a composition solution comprising a vasodilator, an anti-thrombotic agent, an anticoagulant, an antibiotic, a chemotherapeutic agent, or any other therapeutic agents.

According to yet a further embodiment of the invention, a catheter device is provided that includes an elongate catheter body, having a distal end and a proximal end, and also having at least one lumen extending from the proximal end to the distal end of the elongate catheter body. A catheter device according to this embodiment may further include at least one sensor device affixed to the elongate catheter body substantially near the distal end and in electrical communication with a controller, and a fluid delivery device in fluid communication with the at least one lumen and in electrical communication with the controller. The controller may be operable to execute instructions to: receive at least one signal from the at least one sensor device, perform an analysis on the at least one signal, and generate a signal to adjust fluid delivery to the at least one lumen from the fluid delivery device, responsive at least partially to the analysis performed.

An aspect of this embodiment may include a catheter device where the at least one sensor device comprises a pressure sensor device operable to sense pressure in the fluid at or near the distal end of the catheter device. Alternatively, another aspect of this embodiment may include the catheter device where the at least one sensor device comprises a distal sensor device, and further including a proximal sensor device affixed to the elongate catheter body proximal the distal sensor device and in communication with the controller. The distal sensor device may generate a first signal corresponding to a distal pressure and the proximal sensor device may generate a second signal corresponding to a proximal pressure.

For example, the analysis performed by the controller may comprise comparing the distal pressure to the proximal pressure, and wherein if the distal pressure is at a predefined limit greater than the proximal pressure, the signal to adjust fluid delivery causes an increase in the fluid delivery, and wherein if the distal pressure is at a predefined limit lower than the proximal pressure, the signal to adjust fluid delivery causes a decrease in the fluid delivery. In another example, the analysis performed by the controller may include determining a ratio of the distal pressure to the proximal pressure, and wherein if the ratio is at or exceeds a first predefined limit, the signal to adjust fluid delivery causes an increase in the fluid delivery, and wherein if the ratio is below a second predefined limit, the signal to adjust fluid delivery causes a decrease in the fluid delivery. The fluid delivery device may deliver, for example, a vasodilator, an anti-thrombosis agent, a chemotherapy agent, or other therapeutic agent as needed.

According to another aspect of this embodiment, the at least one sensor device may be a flow sensor device operable to assess a flow rate of the fluid at or near the distal end of the catheter device. An aspect of this embodiment may include a catheter device where the at least one sensor device comprises a blood flow transducer operable to monitor and assess blood flow velocity in the major arteries on a real time, beat-to-beat basis at or near the distal end of the catheter device. In certain embodiment, an ultrasound probe may be attached to the primary catheter to monitor blood flow speed thereby discovering the presence of vasospasm.

According to yet another embodiment of the invention, a method for using a catheter device is provided. The method may include sensing by at least one sensor device a condition at at least one location in a vessel in which the catheter is positioned, transmitting at least one signal to a controller from the at least one sensor device corresponding to the condition sensed, performing an analysis on the at least one signal, and adjusting a fluid delivery device in communication with the catheter device responsive at least in part to the analysis performed on the at least one signal. In one example, the method may include sensing a condition substantially near a distal end of the catheter device by a distal sensor device and sensing a condition proximal to the distal end by a proximal sensor device, wherein the analysis includes comparing the condition sensed by the distal sensor device to the condition sensed by the proximal sensor device.

According to one aspect of this embodiment, the fluid delivery may be adjusted by increasing fluid delivery if the condition sensed at the distal sensor device is greater than the condition sensed by the proximal sensor device, and decreasing fluid delivery if the condition sensed at the distal sensor device is lower than the condition sensed by the proximal sensor device.

According to yet another embodiment of the invention, a method for using a catheter device for treating vasospasm is provided. The method may include coating the endovascular catheter of the present invention with an anti-thrombotic agent or anticoagulant, such as heparin, in conjunction with other therapeutic agents, including, but not limited to, antibiotic, vasodilator, and chemotherapeutic agent; inserting the coated endovascular catheter into the appropriate location; and timely releasing the therapeutic agents as needed. In certain embodiments, the method of the present invention uses an endovascular catheter device that comprises a catheter tip that may be fashioned like a shower head with one central lumen in which the wire is used to pass the catheter in the correct position. The catheter tip may include a number of smaller openings that allow fluid comprising one or more therapeutic agents, such as anti-thrombosis agent, anticoagulant, vasodilator, antibiotic, and chemotherapeutic agent, to exit the catheter at a higher pressure. In one embodiment, the catheter of the present invention is a cerebral catheter configured to be inserted into cerebral arteries to prevent and treat cerebral vasospasm, brain neoplasms (e.g., brain glioblastomas), or other pathological conditions associated with prolonged use of a catheter device.

In yet anther embodiment of the invention, the method of the present invention uses an endovascular catheter device that comprises a cybernetic loop for management of cerebral vasospasm in which the distal portion of the catheter is placed in an appropriate location. The method comprises placing a transducer that monitors blood pressure or velocity at a location near the tip of the catheter; placing another transducer located proximally in the systemic circulation which also records blood pressure or velocity; and connecting a pump to the catheter, operable in a cybernetic fashion, wherein the pump increases the flow of a vasodilator or other vasogenic substance into the area of vasospasm when the ratio of the distal blood pressure or velocity and proximal blood pressure or velocity increases, and wherein the pump diminishes the flow of pumping the vasodilator or other vasogenic substance into the area of vasospasm when the ratio between the distal blood pressure or velocity and proximal blood pressure or velocity decreases toward normality. In one embodiment, the vasodilator is verapamil. In yet another embodiment, other therapeutic agents, such as antibiotic and chemotherapeutic agents can also be used in conjunction with the vasodilators or other vasogenic substances to prevent or treat catheter induced infections and neoplasms. The present invention also provides a method of using the catheter devices in conjunction with an externally located blood flow transducer to detect, prevent, and treat vasoplasms, neoplasms, or other pathological conditions associated with prolonged use of the catheter devices.

In yet another embodiment of the invention, the method of the present invention uses any of the above endovascular catheter devices to inject chemotherapeutic agents into neoplasms, particularly those located in the brain such as glioblastomas. The appropriate feeding vessel can be catheterized and the chemotherapeutic agent can be delivered slowly over a prolonged period of time at a routinely programmed rate.

BRIEF DESCRIPTION OF THE DRAWINGS

The objects and advantages of the invention will be better understood and more readily apparent when considered in conjunction with the following detailed description and accompanying drawings which illustrate, by way of example, embodiments of the catheter device and methods of using the same and in which:

FIG. 1A illustrates a partial view of the catheter device, according to one example embodiment of the invention. FIG. 1B illustrates a lateral cross-section view of the catheter device of FIG. 1A, taken across line 1-1, according to one example embodiment of the invention.

DETAILED DESCRIPTION OF THE INVENTION

As required, detailed embodiments of the invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present invention provides a catheter device, and method of use thereof, for preventing and treating vasospasm, formation of thrombosis or other embolic phenomenon, catheter induced infections, and neoplasms.

Catheter devices may be used during neurosurgical procedures for the treatment of conditions existing in the cerebrum. One use of a catheter device during neurosurgical procedures is during the treatment of cerebral vasospasms. For example, a catheter may be used to selectively deliver a vasodilating agent to the vasospastic site. In another example, a catheter may be used to mechanically dilate the vessel, such as by the use of a balloon tip during angioplasty procedures. Though, because of the potential that the catheter may become thrombosed during the procedure, limiting the duration of catheter use in the patient, the above-mentioned therapeutic procedures have been limited. Often, the duration during which the catheter should be inserted for optimum treatment is longer than a safe period to avoid causing thrombosis in the vasculature.

A catheter device for use in neurosurgical procedures (as well as other procedures), as described herein, has been developed to overcome the difficulties previously described. The catheter device may include a coating or a matrix layer comprising protein or other anti-thrombotic agents infused therein. In one example, the anti-thrombotic coating or layer may include a time-release mechanism, whereby the release of the anti-thrombotic agent may be controlled over time. The coating may be applied at least partially to the exterior surface of the catheter device, and optionally may be applied to at least partially to the interior surface of the catheter making up one or more lumens or ports. It is appreciated that additional medicinal agents may be included in the coating or layer, such as, but not limited to, antibiotics, aspirin, heparin, warfarin, anticoagulants, vasodilators, or chemotherapeutic agents. The anti-thrombotic agent (or other coating) may be impregnated into the catheter device via a protein colloidal matrix.

As used herein, anti-thrombotic agents are used interchangeably with anticoagulant, both refer to therapeutic agents that are capable of preventing and/or treating thrombosis and embolic phenomenon. Thrombosis refers to a formation of a blood clot (thrombus) inside a blood vessel, obstructing the flow of blood through the circulatory system. Embolisation occurs when a bacterial infection is present at the site of thrombosis, the thrombus may break down, spreading particles of infected material throughout the circulatory system (pyemia, septic embolus) and setting up metastatic abscesses wherever they come to rest. Without an infection, the thrombus may become detached and enter circulation as an embolus, finally lodging in and completely obstructing a blood vessel, which unless treated very quickly will lead to tissue necrosis (an infarction) in the area past the occlusion. If the occlusion is in the coronary artery, myocardial ischemia is likely to occur, whereby cardiac myocytes cannot function properly due to lack of oxygen. This lack of oxygen is then likely to result in a myocardial infarction. A stroke is cause by cerebral infarction resulted from a disturbance in the blood vessels supplying blood to the brain. Exemplary anti-thrombolic agents or anticoagulants include, but are not limited to, heparin and derivative substances including low molecular weight heparin, vitamin K antagonist, warfarin, and derivative substances, and synthetic pentasaccharide inhibitors of factor Xa such as fondaparinux and idraparinux.

As used herein, vasodilators refer to drugs that relax the smooth muscle in blood vessels, which causes the vessels to dilate. Vasodilators can be classified based on their site of action (arterial versus venous) or by mechanism of action. Some vasodilators primarily dilate resistance vessels (arterial dilators; e.g., hydralazine), while others primarily affect venous capacitance vessels (venous dilators; e.g., nitroglycerine). Most vasodilator drugs, however, have mixed arterial and venous dilator properties (mixed dilators; e.g., alpha-adrenoceptor antagonists, angiotensin converting enzyme inhibitors). In one embodiment, the vasodilator is verapamil.

In another example embodiment, the catheter device may also include a perforated tip connected to its distal end or distal region. The perforated tip may provide an improved distribution of fluid flow from within the catheter. Additionally, the perforated tip may allow fluid to be delivered to the site at a higher pressure. By increasing the fluid flow and/or increasing the pressure at which the fluid is delivered, clotting will be reduced at the site. The fluid being delivered may be, in one example, a saline solution. In another example, the fluid being delivered may be, either alone or in combination with other fluids comprising other therapeutic agents, such as an anti-thrombotic agent or other anticoagulant to reduce the likelihood of forming a thrombus at the site or on the catheter, a vasodilator to treat vasospasms occurring at the site, an antibiotic to treat catheter-induced local or systemic infections, or a chemotherapeutic agent to treat neoplasm. Furthermore, it is appreciated that this embodiment may further include an anti-thrombotic agent coating on all or part of the surface of the catheter body and optionally on the interior surface of the catheter making up the lumen.

In another example embodiment, the catheter device may include at least one sensor device positioned at or near the distal portion of the catheter device. In one example, the sensor device may be a pressure or blood flow velocity sensor device. The pressure sensor device may communicate the pressure existing in the vessel near the distal portion of the catheter to an adjustable controller, which may then adjust the delivery of a vasodilator to the site based upon the pressure measured. The combination of one or more pressure sensing devices in communication with the controller may allow for implementing a feedback loop (or cybernetic loop) between the pressure sensed at the site (for example, the vasospasm site) and the delivery of the agent and/or any other fluids to the site. For example, the greater the pressure, the greater the delivery of the vasodilator to the site. Alternatively, sensing a decreased or a decreasing pressure at the site may cause the controller to deliver less vasodilator.

In another embodiment, the catheter device may include two pressure sensing devices, both in communication with a controller. The first pressure sensing device may be positioned at or near the catheter's distal portion, as previously described, and the second pressure sensing device may be positioned proximal from the first pressure sensing device, for example in the systemic vasculature. Having two pressure sensing devices allows for the controller to perform a relative comparison between the pressure measured in the vasculature at or near the procedure site and the pressure at another point in the patient's vasculature. The relative comparison allows the controller to adjust the delivery of the vasodilator (or other agents) based on the difference between the two measured pressures. It is appreciated that the two measured pressures may be compared in many ways, for calculating the difference, calculating a ratio, modeling, adaptive, real-time learning, mathematical algorithms, or the like. It is also appreciated that the operator of the catheter, for example the physician performing the procedure, may also observe the measured pressure at the first or both the first and the second locations as displayed by the controller and perform the adjustments manually.

The catheter device may also include, in addition to or alternatively, other sensing devices at or near the distal portion of the catheter to aid in sensing the environment at or near the procedure site. In one example embodiment, the catheter device may include an ultrasonic monitoring device at or near the distal portion of the catheter device and in communication with a controller. The ultrasonic monitoring device may be used to monitor blood flow rate at or near the site, which may be indicative of the presence and/or severity of a vasospasm in the vessel. As described in reference to the pressure sensing devices, the flow rate measurements obtained from the ultrasonic monitoring device may be supplied to the controller for adjusting the delivery of fluid, such as vasodilators, or alter other treatment being provided by the catheter. It is appreciated that these embodiments including sensor devices may further include an anti-thrombotic agent coating on all or part of the surface of the catheter body and optionally on the interior surface of the catheter making up the lumen.

In one embodiment, an ultrasonic monitoring device is a transducer that is implanted, recessed into, or temporarily attached to patient's skull. Such a transducer can be used in conjunction with the cerebral catheter of the invention to assess blood flow velocity in the major basal intracranial arteries on a real-time, beat-to-beat basis. Blood flow velocity is calculated and used to make determinations about intracranial hemodynamics. The blood flow velocity obtained from the ultrasonic transducer can be supplied to the controller for adjusting the delivery of the therapeutic fluid comprising desired therapeutic agents as described above, particularly for treating cerebral vasospasms, thrombotic and embolic phenomenon, catheter-induced infections, or neoplasms. The neurological or cerebral catheters of the invention are particularly configured to be inserted into major intracranial arteries before, during, or after neuro- and/or brain surgery. Methods of implanting or attaching the transducer to the patient's skull are well known in the art. For instance, the transducer attached to a helmet or a head-band that can be wore by the patient. The transducer can also be implanted or screwed onto patient's skull.

In one embodiment, the ultrasonic transducer used in conjunction with the catheter device of the invention can be a Transcranial Doppler (TCD) (developed by Multigon, Texas). The cranial catheters of the present invention in conjunction with TCD can be used to evaluate intracranial effects of extracranial lesions, including information on collateralizing channels and tandem stenoses. In addition, the cranial catheters of the present invention in conjunction with TCD allows direct perioperative evaluation of middle cerebral artery blood flow velocity in carotid endarterectomy patients, and to monitor for re-occlusion and hyperperfusion syndrome. Furthermore, the cranial catheters of the present invention in conjunction with TCD is also used to detect and classify intracranial emboli in view of the appearance of high intensity transient signals in the TCD waveform as indicators of circulating microemboli. Other applications of the cranial catheters of the present invention in conjunction with TCD also include the early (sub-angiographic) bedside detection of vasospasm in subarachnoid hemorrhage patients, evaluation of stroke and transient ischemic attack, as an adjunct in the assessment of cerebral circulatory arrest, and as a monitoring tool for patients undergoing intracranial interventional procedures. The present invention also encompasses the use of the additional catheter devices, particularly neurological or cerebral catheter devices, in conjunction with other blood flow transducers or diagnostic modalities, for monitoring and assessing intracranial hemodynamics, allowing a physician or controller for adjusting timely release or delivery of appropriate therapeutic agents at the catheter site over an extended period of time.

Although the catheter device has been described in detail above as delivering a vasodilator and/or anti-thrombotic agent, it is appreciated that other medicinal and/or therapeutic agents may be delivered by the catheter device in much the same manner as described herein. Therefore, in one embodiment, the catheter device may be used to aid in the delivery of chemotherapeutic agents, such as a bevacizumab, to neoplasms or other tumorous conditions. A catheter device having a coating or layer of anti-thrombotic agents applied to its elongate body, or configured to deliver anti-thrombotic agents to the site, as further described herein for extended indwelling, allows for longer duration procedures and more effective delivery of chemotherapeutic agents. In one example, the catheter device may be configured to deliver chemotherapeutic agents to the glioblastoma sites. Though, it is appreciated that a catheter configured for the delivery of chemotherapeutic agents may be used for any type of neoplasm or tumorous condition, and is not limited by this example description to glioblastoma sites. The examplary catheter device may inserted and directed to the neoplasm site, and used to deliver one or more chemotherapeutic agents over longer durations than were previously available. Furthermore, the chemotherapeutic agent may be released over time to the neoplasm site or in periodic dosages, such as on for a predefined period and off for a predefined period and back on, over time. The catheter device may also be configured to communicate with a controller to control the delivery of the chemotherapeutic agent. An anti-thrombotic layer or coating may allow keeping the catheter inserted for longer periods of time, allowing for longer durations of chemotherapeutic agent administration.

Example catheter devices can further be understood with reference to the example, non-limiting embodiments illustrated in FIGS. 1-4.

Figure 1A:
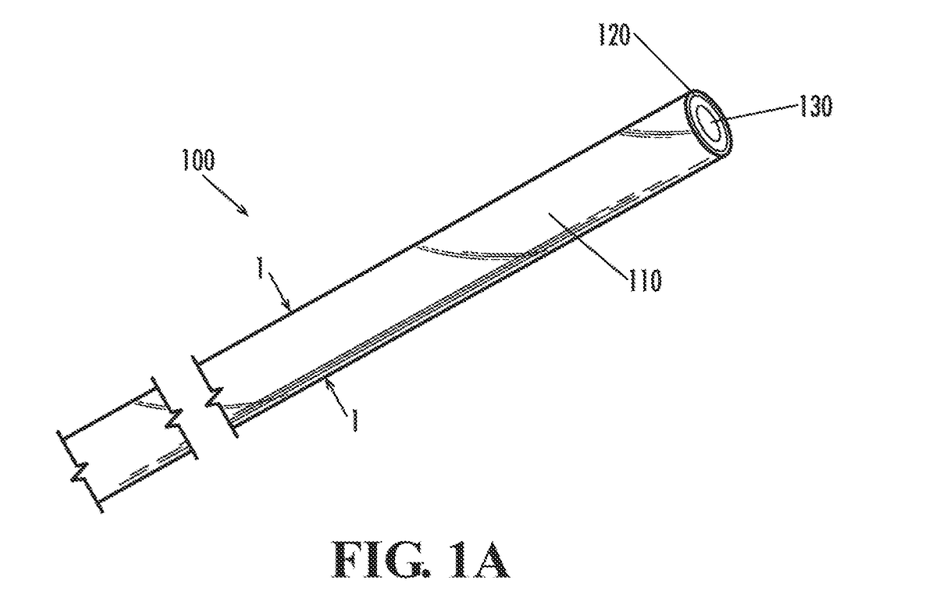
FIGS. 1A-B are schematic views of the catheter device, according to one example embodiment of the invention.

FIG. 1A illustrates an example embodiment of a catheter device 100 including an anti-thrombotic agent coating or layer on its exterior surface. The catheter device 100 may be an elongate catheter body 110 for insertion through a patient's vasculature and delivery to a disease or symptomatic site. In one example, the catheter device 100 may be used during the treatment of a vasospasm in a vessel. The vasospasm may exist, for example, in the patient's cerebral vasculature. The elongate catheter body 110 may be constructed from a semi-rigid to pliable material to ease both in the insertion and guiding to the procedure site. For example, the elongate catheter body 110 may be constructed from a material that is substantially rigid at room temperature, but becomes pliant as exposed to higher temperatures, such as the patient's body temperature. The catheter body 110 may optionally include material that causes the catheter device 100 to be radiopaque and/or include one or more markers such as fluoroscopic or radiopaque markers used to help locate and guide the catheter.

It is appreciated that the size of the elongate catheter body 110 may vary, depending upon its intended use. In one example, a catheter device 100 intended for delivery to the cerebral vasculature may have a diameter between approximately 0.25 millimeters and approximately 1.0 millimeters (or, for example, approximately 1 Fr. to 3 Fr.). However, it is appreciated that other catheter devices used with this invention may have greater or smaller diameters. The catheter device may be inserted through a femoral artery or subclavian vein. In some example embodiments, the catheter device is delivered to the cerebral vasculature, for example the distal portion of the carotid artery, for the treatment of cerebral vasospasms and the like.

The catheter device 100 may further include an anti-thrombotic agent coating 120 on its exterior surface, or alternatively an anti-thrombotic agent layer as the exterior surface may be formed as part of the catheter device. The anti-thrombotic agent coating/layer 120 may include, for example, heparin, or a mixture of heparin and other treatment agents or substances. In one example, in addition to anti-thrombotic agents, one or more antibiotic substances may be included in the layer 120. In another example, the anti-thrombotic agent coating 120 may be formed as part of a matrix, for example, a protein matrix, a colloidal matrix, or a protein colloidal matrix, as is known. The anti-thrombotic layer 120 may be applied to substantially the entire length of the catheter, or may be applied only to specific areas in which the likelihood of thrombosis are greater. In another example, an additional anti-thrombotic layer may be at least partially applied to the interior surface of the catheter device 100. Including an anti-thrombotic layer in the interior surface of the catheter device 100 allows for the release of the agent as fluid or other devices are delivered therethrough. Additionally, the anti-thrombotic coating or layer may include a time-release mechanism, whereby the release of the anti-thrombotic agent may be controlled over time.

The anti-thrombotic agent allows for keeping the catheter device inserted for prolonged periods, making available additional procedures and treatments. For example, a time released anti-thrombotic agent coating or layer may allow for using the catheter device in patient for up to approximately ten days. In some applications, for example during neurosurgical procedures, a catheter device including an anti-thrombotic agent may be inserted before or during the neurosurgical procedure, to allow detecting and treating a vasospasm. Alternatively, a catheter may be inserted immediately after a procedure, or after a certain period during which the risk of forming vasospasms increases. For example, after a neurosurgical procedure, the risk of forming vasospasms may increase at or around 4 days after the procedure. Accordingly, a catheter coated with an anti-thrombotic agent may be inserted near that time and left in for multiple days to treat the onset of a vasospasm. It is further appreciated that other aspects of this invention, for example the one or more sensors as described below in reference to FIG. 3, may further facilitate near instantaneous detection of a vasospasm by a catheter device already existing in the patient's vasculature.

Figure 1B:
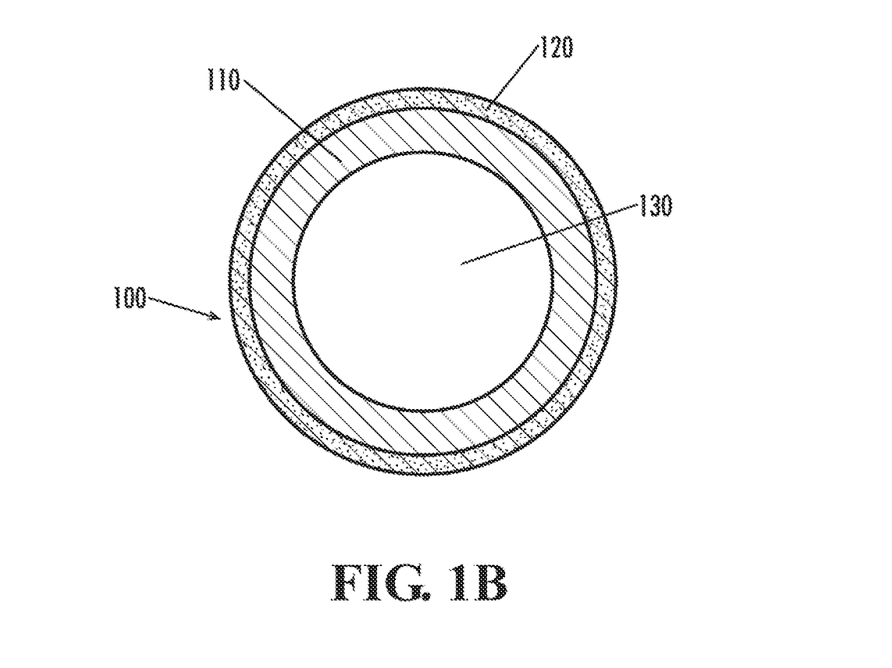

FIG. 1B illustrates a lateral cross-section diagram of an example catheter device 100 taken across line 1-1. Accordingly, the catheter device 100 may include one or more lumens 130 existing therein. The lumen or lumens (also known as ports) 130 may be used for fluid delivery such as medicinal agents, protein solutions, additional anti-thrombotic agent delivery, vasodilating agent, or the like, or for delivery of secondary devices such as guide wires used to aid insertion, balloons or other devices used during angioplasty, sensors, or the like. It is appreciated that although FIG. 1B illustrates a single lumen, the catheter device 100 may be configured to include multiple lumens. The catheter device 100 illustrated in FIG. 1B includes an anti-thrombotic agent coating or layer 120.

In the illustrated embodiment, the coating 120 may be applied around the entire circumference of the elongate catheter body 110. However, it is appreciated that the anti-thrombotic agent coating 120 may only be applied to portions of the catheter's surface, such as strips aligning axially with the elongate catheter body 110 or in rings around all or part of the circumference of the elongate body and positioned at one or more portions along the length of the elongate catheter body 110. Again, the anti-thrombotic agent 120 may be applied as a coating to all or part of the exterior surface, may be impregnated in the material comprising the surface of the elongate catheter body 110, may be applied as part of a matrix, such as a protein, colloid, or protein colloidal matrix, and/or may be applied to the interior surface of the catheter device 100 defining the one or more lumens 130.

Figure 2:
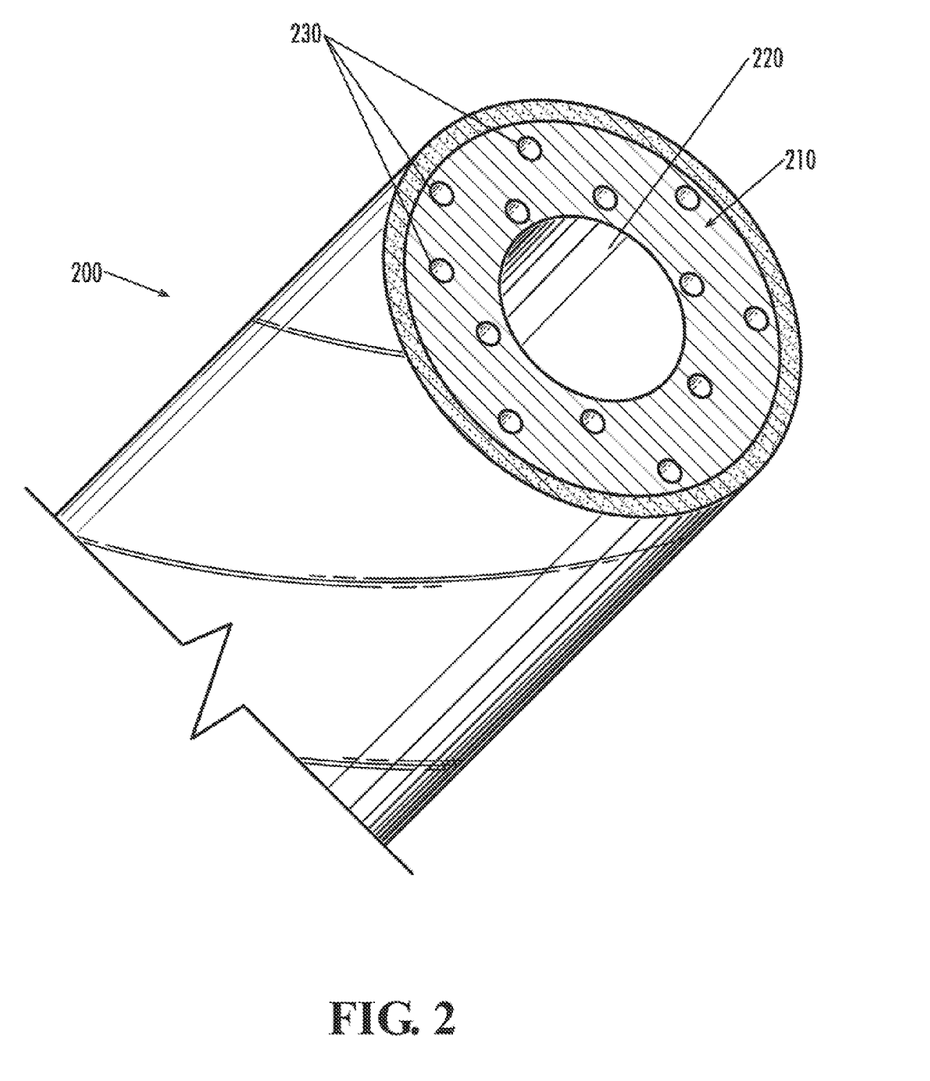
FIG. 2 illustrates a partial distal end view of the catheter device, according to one example embodiment of the invention.

FIG. 2 illustrates another example embodiment of the catheter device 200 including a perforated tip 210 at its distal end. The perforated tip 210 may be inserted into the elongate catheter body so as to be flush with the body, may be inserted over the elongate catheter body. The perforated tip 210 may be rounded or substantially planar. The perforated tip 210 may include one or more central orifices 220 extending entirely through the tip and in communication with the one or more lumens or ports of the catheter device 200, as further described above in reference to FIG. 1B. For example, the one or more central orifices 220 may communicate with a lumen used with guide wire insertion, or with a lumen used to deliver a secondary device, such as a balloon. It is appreciated that the central orifice or orifices 220 need not align in the center of the perforated tip 210, but instead are to align with the one or more lumens of the catheter used for objects or substances that are not intended to be delivered via the multiple perforated orifices. It is further appreciated that while secondary devices or objects are described as being delivered through the central orifice 220, fluids such as medicinal or therapeutic agents may also be delivered through the one or more central orifices 220. It is further appreciated that another example embodiment may not include a central orifice 220, and only include the multiple perforated orifices as described. The perforated tip 210 further includes multiple perforated orifices 230 extending entirely through the tip, having a diameter substantially smaller than the overall diameter of the elongate catheter body. The multiple perforated orifices 230 may be randomly aligned or aligned in a pattern on the perforated tip 210 for facilitating fluid flow. The multiple perforated orifices 230 may communicate with at least one lumen existing within the catheter device 200.

The perforated tip 210 may facilitate an improved distribution of fluid flow from within the catheter device 200. Additionally, the perforated tip 210 may allow fluid to be delivered to the site at a higher pressure and/or flow velocity. By increasing the fluid flow and/or increasing the pressure at which the fluid is delivered, clotting may also be reduced at the site. The fluid being delivered may be, in one example, a saline solution delivered at rates between approximately 5 cc/hr and approximately 50 cc/hr. In other examples, the fluid delivered may be a vasodilator, such as verapamil, an anti-thrombotic coating, such as heparin, another anticoagulant substance, or any combination thereof. It is appreciated that the perforated tip 210 may also be removably attached to the catheter device 200, allowing for selective use and retrofitted adaptations of the tip to existing catheters.

Figure 3:
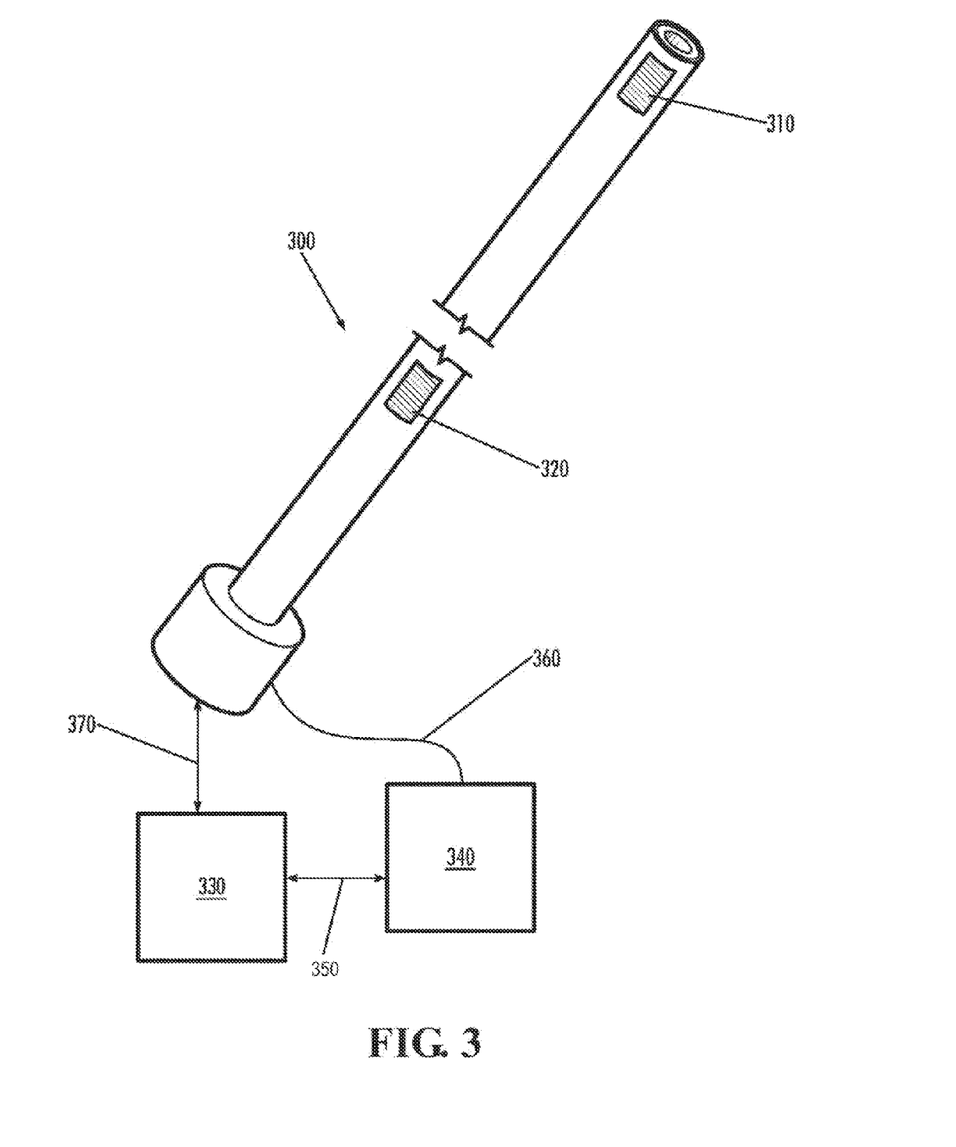
FIG. 3 is a functional diagram of the catheter device, according to another example embodiment of the invention.

FIG. 3 illustrates another example embodiment of the catheter device including at least one sensor and communicating with a controller and a fluid delivery system. The catheter device 300 illustrated in FIG. 3 includes at least one distal sensor device 310, which may be a pressure sensing device, affixed to the elongate catheter body 380 at or near its distal portion for measuring the pressure within the vessel existing at or near the site. The sensor device 310 may be affixed to the elongate catheter body 380 so as to substantially circumscribe the body, or may be affixed at on or more points around the circumference of the elongate catheter body 380. Alternatively, the sensor device 310 may be a single sensor device affixed at a single point on the elongate catheter body 380. In yet another example embodiment, the distal sensor device 310 may be affixed, at least partly, to the tip of the catheter device 300.

The distal sensor device 310 may be, for example, a pressure transducer, a strain gauge, mechanical deflection sensor, piezoresistive/semiconductor, microeletromechanical sensor, vibrational sensor, capacitance-based sensor, fiber optic-based sensor, or the like. The distal sensor device 310 may be in electrical or mechanical communication 370 (depending upon the type of pressure sensor employed) with a controller 330 for transmitting signals corresponding to a pressure sensed in the vasculature. The controller 330 may be computer-based controller, having a memory and a processor for executing software and/or hardware-based instructions for catheter operations and functions, as described more fully herein.

Additionally, the catheter device 300 may be in fluid communication with a fluid delivery system 340 by a fluid path 360 and the controller 330 may be in electrical communication with the fluid delivery system 340 by a communication link 350. The fluid delivery system may be controlled in part by the controller to deliver fluids via the catheter device 300. The distal sensor device 310 in communication with the controller 330 allows for implementing a feedback loop (or cybernetic loop) between the pressure sensed at the site (for example, the vasospasm site) and the delivery of the agent and/or any other fluids from the fluid delivery system 340 to the site. For example, the greater the pressure, the greater the delivery of the vasodilator to the site. Alternatively, sensing a decreased or a decreasing pressure at the site may cause the controller to deliver less vasodilator.

The catheter device may optionally include a proximal sensor device 320 positioned proximally to the distal pressure sensor 310. The proximal sensor device 320 may be positioned at a position on the elongate catheter body 380 so as to be located in the systemic vasculature of the patient. As described above with reference to the distal sensor device 310, the proximal sensor device is in communication with the controller 330 for transmittal signals indicating the pressure at a second point in the patient's vasculature. A catheter device 300 configured with two pressure sensing devices 310, 320 allows the controller 330 to perform a relative comparison of the signals representing the pressure sensed in the vasculature at or near the procedure site and the pressure sensed at another point in the patient's vasculature. The relative comparison allows the controller 330 to adjust the delivery of fluid, for example a vasodilator (or other medicinal agent), based at least in part on two sensed pressures. It is appreciated that the signals representing the two sensed pressures may be compared in many ways, for example, calculating the difference, calculating a ratio, modeling, adaptive, real-time learning, mathematical algorithms; or the like. It is also appreciated that the operator of the catheter device 300, for example a physician performing the procedure, may also observe the measured pressure at the first or both the first and the second locations as displayed by the controller and adjust the fluid delivery system 340 manually, or alter the automatic fluid delivery manually, responsive to the observations.

These example embodiments of a catheter device 300 including one or more sensor devices may further include an anti-thrombotic agent or other anticoagulant coating, as is described more fully with reference to FIG. 1. The inclusion of the anti-thrombotic or anticoagulant coating with a catheter device having one or more sensor devices allows for instantaneous or near-instantaneous detection of vasospasmic activities, and thus further allows for quicker provision of treatment in response thereto.

It is appreciated that the sensor devices 310, 320 need not be pressure sensing devices. For example, the sensor devices may include an ultrasonic sensor device in communication with the controller 330. The ultrasonic sensor device may be used to monitor blood flow at or near the site, which may be indicative of the presence and/or severity of a vasospasm in the vessel. As described in reference to the pressure sensing devices, the signals obtained from the ultrasonic monitoring device representing blood flow may be supplied to the controller 330 for adjusting the delivery of fluid by the fluid delivery device 340. Further, it is appreciated that the signals from any alternative sensor devices may also be displayed, graphically and/or numerically, to the user by the controller 330.

Figure 4:
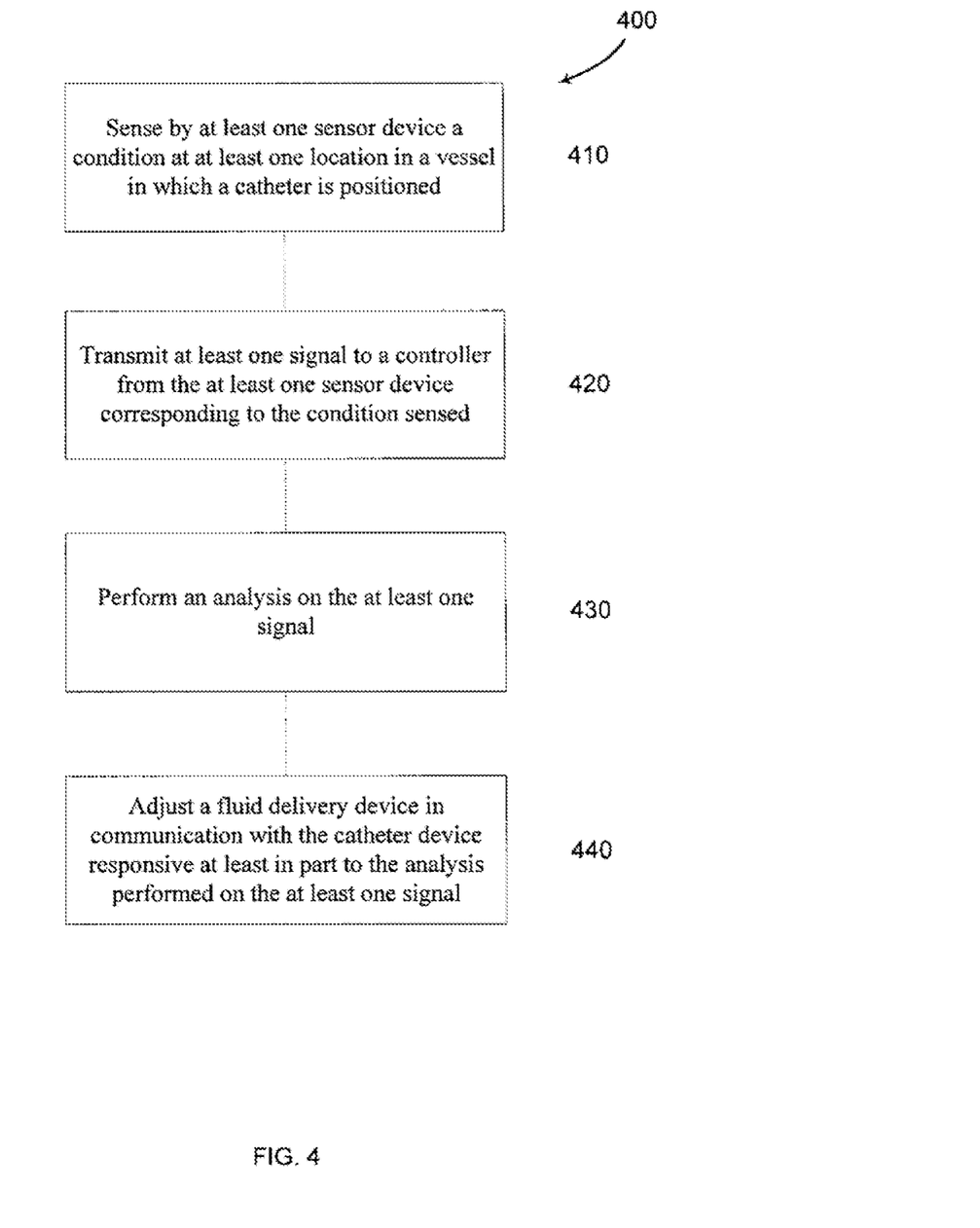
FIG. 4 is a functional flow diagram representing a method of operating the catheter device, according to an example embodiment of the invention.

FIG. 4 illustrates an example method by which an embodiment of the catheter device may operate. Provided is a flowchart 400 illustrating the sensing of a condition at one or more locations in the vasculature and controlling fluid delivery in response thereto, as is described in reference to FIG. 3. In one example, as described above, the condition may be pressure within the vessel, and pressure will be used as the exemplary condition with reference to the method described in FIG. 4. However, it is appreciated that other conditions may be sensed, in addition to or alternatively, and the fluid delivery may be controlled in much the same manner. For example, blood flow may be an alternative condition sensed.

At block 410, pressure is measured at at least one location in the vessel in which the catheter is positioned by one or more sensor devices. The sensor device may be a pressure transducer, or the like. Furthermore, in some example embodiments, the pressure may be sensed at two locations—at or near the distal portion of the catheter (e.g., distal sensor device) and proximal to that portion (e.g., proximal sensor device)—allowing for a comparison of the two pressures for controlling fluid delivery.

Block 420 follows block 410, in which a signal is transmitted from the one or more pressure sensor devices to a controller. The signal transmitted may be a raw digital signal which may be operated on to generate meaningful units at the controller, as is known.

Block 430 follows block 420, in which the controller performs an analysis on the one or more signals received from the sensor device. For example, if the catheter device includes one sensor device—a distal sensor device—the controller may simply compare the pressure to known pressure ranges to determine whether the pressure is within an acceptable range. Alternatively, the controller may compare to previously received and stored pressure measurements to determine the direction in which the pressure is moving. If the catheter device includes two sensor devices—a distal sensor device and a proximal sensor device—the analysis performed at block 430 may include comparing between the two pressures sensed, as described above.

Block 440 follows block 430, in which the fluid delivered through the catheter device is adjusted based at least in part on the analysis of signals received from the one or more sensor devices, as performed at block 430. In one embodiment, the controller may automatically perform the adjustment responsive to the analysis performed. In another embodiment, the operator of the catheter, for example a physician, may perform the adjustment based upon a display of the result of the analysis performed at block 430 and/or a display of the condition measurement corresponding to the signal transmitted from the sensor devices. It is also appreciated that while the fluid delivery may be automatically controlled by the controller, an operator may also adjust the delivery manually. An example of adjusting the fluid delivery as performed at block 440 may be increasing the delivery of a vasodilator when the analysis determines the pressure is increasing, or decreasing the delivery of the vasodilator when the analysis determines that the pressure is decreasing.

In another example including a distal sensor device and a proximal sensor device, the analysis performed at block 430 may result in a ratio comparing the signals transmitted from the distal sensor device to the signals transmitted from the proximal sensor device, whereby if the ratio is over a predefined number (e.g., greater than around 1:1), then the controller causes the fluid delivery device to deliver greater amounts of vasodilating fluid to the site. Similarly, if the ratio is lower than a predefined number, then the controller may reduce or halt the delivery of vasodilating fluid to the site. The controller may further include instructions that allow increases the rate at which the fluid is delivered based on the signals received from the one or more sensor devices. For example, the greater the disparity between the signal from the distal sensor device and the signal from the proximal sensor device, the greater the rate the controller causes the fluid delivery device to deliver vasodilating fluid. It is appreciated that the predefined limits or thresholds may be predetermined during the manufacture and/or configuration of the catheter device, or may be set by an operator or configurator after manufacture and before or during use. Furthermore, any predefined limits or thresholds for use in the analysis may be adjustable and set through an interface or the like.

References are made to block diagrams of systems, methods, apparatuses, and computer program products according to example embodiments of the invention. It will be understood that at least some of the blocks of the block diagrams, and combinations of blocks in the block diagrams, respectively, may be implemented at least partially by computer program instructions. These computer program instructions may be loaded onto a general purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the block or blocks. The computer program instructions may also be loaded onto a computer or other programmable data processing apparatus to cause a series of operational elements to be performed on the computer or other programmable apparatus to produce a computer implemented process such that the instructions that execute on the computer or other programmable apparatus provide elements for implementing the functions specified in the block or blocks.

One or more components of the systems and one or more elements of the methods described herein may be implemented through an application program running on an operating system of a computer. They also may be practiced with other computer system configurations, including hand-held devices, multiprocessor systems, microprocessor based, or programmable consumer electronics, mini-computers, mainframe computers, etc.

Application programs that are components of the systems and methods described herein may include routines, programs, components, data structures, etc. that implement certain abstract data types and perform certain tasks or actions. In a distributed computing environment, the application program (in whole or in part) may be located in local memory, or in other storage. In addition, or in the alternative, the application program (in whole or in part) may be located in remote memory or in storage to allow for circumstances where tasks are performed by remote processing devices linked through a communications network.

Many modifications and other embodiments of the invention set forth herein to which these descriptions pertain will come to mind having the benefit of the teachings presented in the foregoing descriptions and the associated drawings. Thus, it will be appreciated that the invention may be embodied in many forms and should not be limited to the example embodiments described above. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A catheter device, comprising:
   an elongate catheter body, comprising a distal end and a proximal end;
   at least one lumen extending from the proximal end to the distal end of the elongate catheter body;
   a distal sensor device affixed to the elongate catheter body substantially near the distal end, wherein the distal sensor device generates a first signal that is a distal pressure or flow rate;
   a proximal sensor device affixed to the elongate catheter body proximal the distal sensor device and configured to be positioned in a patient's systemic vasculature, wherein the proximal sensor device generates a second signal that is a proximal pressure or flow rate;
   a controller in communication with the proximal and distal sensor devices, and
   a fluid delivery device in fluid communication with the at least one lumen and in electrical communication with the controller;
   wherein said catheter device is a cerebral catheter device configured to be inserted into cerebral arteries;
   wherein the controller is configured to perform an analysis comprising comparing:
   the first and second signals generated from the distal and proximal sensor devices, and cause an
   (a) increase in fluid delivery to the at least one lumen from the fluid delivery device if the distal pressure or flow rate is at a first predefined limit greater than the proximal pressure or flow rate, or
   (b) decrease in fluid delivery to the at least one lumen from the fluid delivery device if the distal pressure or flow rate is at a second predefined limit lower than the proximal pressure or flow rate.

2. The catheter device of claim 1, wherein the analysis performed by the controller comprises determining a ratio of the distal pressure or flow rate to the proximal pressure or flow rate, and wherein if the ratio is at or exceeds a first predefined ratio limit, the fluid delivery is adjusted to be increased, and wherein if the ratio is below a second predefined ratio limit, the fluid delivery is adjusted to be decreased.

3. The catheter device of claim 2, wherein the first predefined ratio limit and the second predefined ratio limit comprise the same value.

4. The catheter device of claim 1, wherein the fluid delivery device delivers a fluid comprising at least a saline solution comprising a vasodilator, an anti-thrombotic agent, an antibiotic, a chemotherapeutic agent, other suitable therapeutic agent, or combination thereof.

5. The catheter device of claim 4, wherein said anti-thrombotic agent is selected from the group consisting of heparin, warfarin, synthetic pentasaccharide inhibitors of factor Xa, and derivatives thereof.

6. The catheter device of claim 4, wherein said vasodilator is verapamil.

7. The catheter device of claim 1, further comprising an anti-thrombotic agent at least partially coated or deposited thereon.

8. The catheter device of claim 7, wherein the anti-thrombotic agent comprises a coating applied to substantially an entire surface of the elongate catheter body.

9. The catheter device of claim 7, wherein the anti-thrombotic agent is at least partially impregnated into the elongate catheter body.

10. The catheter device of claim 7, wherein the anti-thrombotic agent is deposited at least partially in an interior surface of the catheter device comprising the at least one lumen.

11. The catheter device of claim 7, wherein the anti-thrombotic agent is time releasable.

12. The catheter device of claim 1, wherein the distal end of the catheter device further comprises a perforated tip affixed thereon, wherein the perforated tip comprises a rounded or substantially planar surface on a distal end of the perforated tip, and a plurality of perforated orifices on the rounded or substantially planar surface and extending through the perforated tip and in fluid communication with the at least one lumen.

13. The catheter device of claim 12, wherein the at least one lumen comprises a first and a second lumen, wherein the plurality of perforated orifices further comprise at least one central orifice in communication with the first lumen, and wherein the plurality of perforated orifices other than the at least one central orifice are in fluid communication with the second lumen.

14. The catheter device of claim 13, further comprising a secondary medical device passed through the first lumen and the at least one central orifice, wherein the secondary medical device comprises one of a guide wire and a balloon.

15. The catheter device of claim 12, wherein a fluid is delivered through the at least one lumen and the plurality of perforated orifices, wherein the fluid comprises at least one of a saline solution comprising a vasodilator, an anti-thrombotic agent, an antibiotic, a chemotherapeutic agent, other suitable therapeutic agent, or combination thereof.

16. The catheter device of claim 12, wherein the perforated tip is inserted into or is inserted over the elongate catheter body.

17. A method for preventing and treating vasospasm using the catheter device of claim 1.

18. The method of claim 17, wherein said catheter device is used in conjunction with a blood flow transducer operable to detect a blood flow velocity and a presence of vasospasm.

19. The method of claim 18, wherein said blood flow transducer is an ultrasonic monitoring device.

20. The method of claim 18, wherein said blood flow transducer is implanted, recessed into, screwed onto, or temporarily attached to the patient's skull.

21. The method of claim 18, wherein the blood flow velocity obtained from the blood flow transducer is supplied to the controller for adjusting delivery of a therapeutic fluid comprising a desired therapeutic agent.

22. A method for treating neoplasm using the catheter device of claim 1.

23. The method of claim 22, wherein said neoplasm is brain glioblastomas.

24. The catheter device of claim 1, wherein the controller includes instructions to increase a rate of the fluid delivery based on at least one of the first and second signals from at least one of the proximal and distal sensor devices.

25. The catheter device of claim 24, wherein the rate of fluid delivery increase is proportional to a difference between the first signal from the distal sensor device and the second signal from the proximal sensor device.

* * * * *